US009958433B2

(12) United States Patent
Yu et al.

(10) Patent No.: US 9,958,433 B2
(45) Date of Patent: May 1, 2018

(54) METHOD AND SYSTEM FOR IN VITRO DEVELOPMENTAL TOXICITY TESTING

(71) Applicant: Agency for Science, Technology and Research, Singapore (SG)

(72) Inventors: Hanry Yu, Singapore (SG); Yi-Chin Toh, Singapore (SG); Jiangwa Xing, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 20 days.

(21) Appl. No.: 14/432,041

(22) PCT Filed: Sep. 30, 2013

(86) PCT No.: PCT/SG2013/000426
§ 371 (c)(1),
(2) Date: Mar. 27, 2015

(87) PCT Pub. No.: WO2014/051525
PCT Pub. Date: Apr. 3, 2014

(65) Prior Publication Data
US 2015/0276711 A1    Oct. 1, 2015

(30) Foreign Application Priority Data
Sep. 28, 2012 (SG) ............... 201207242-7

(51) Int. Cl.
*G01N 33/50* (2006.01)

(52) U.S. Cl.
CPC ..... *G01N 33/5014* (2013.01); *G01N 33/5026* (2013.01); *G01N 33/5044* (2013.01); *G01N 33/5073* (2013.01)

(58) Field of Classification Search
CPC ........... G01N 33/5044; G01N 33/5026; G01N 33/5014; G01N 33/5073
See application file for complete search history.

(56) References Cited

U.S. PATENT DOCUMENTS

2010/0166713 A1* 7/2010 Dalton ................ C12N 5/0603
424/93.7

FOREIGN PATENT DOCUMENTS

| CN | 101622537 A | 1/2010 | |
|---|---|---|---|
| CN | 101641436 A | 2/2010 | |
| CN | 102089658 A | 6/2011 | |
| EP | 2180042 A1 * | 4/2010 | ........... C12N 5/0068 |
| WO | WO 2008/094597 A2 | 8/2008 | |
| WO | WO 2008/107912 A2 | 9/2008 | |
| WO | WO 2014/051525 A1 | 4/2014 | |

OTHER PUBLICATIONS

Singh et al., Tissue Engineering, 14(4): 341-366, 2008.*
Bakre et al., J of Biol. Chemistry, 282(43): 31703-31712, 2007.*
Chinese Office Action for Application No. 201380050957.0 dated Aug. 26, 2016.
International Search Report and Written Opinion for PCT/SG2013/000426 dated Dec. 23, 2013.
International Preliminary Report on Patentability for PCT/SG2013/000426 dated Apr. 9, 2015.
Bauwens et al., Control of human embryonic stem cell colony and aggregate size heterogeneity influences differentiation trajectories. Stem Cells. Sep. 2008;26(9):2300-10. doi: 10.1634/stemcells.2008-0183. Epub Jun. 26, 2008.
Jagtap et al., Cytosine arabinoside induces ectoderm and inhibits mesoderm expression in human embryonic stem cells during multilineage differentiation. Br J Pharmacol. Apr. 2011;162(8):1743-56. doi: 10.1111/j.1476-5381.2010.01197.x.
Lee et al., Micropatterning of human embryonic stem cells dissects the mesoderm and endoderm lineages. Stem Cell Res. Mar. 2009;2(2):155-62. doi: 10.1016/j.scr.2008.11.004. Epub Dec. 3, 2008.
Luo et al., Cell patterning technology and its application in the research of embryonic stem cells. Journal of Analytical Science. Aug. 31, 2011; 4(27):519-524. Abstract Only.
Mehta et al., Assessment of drug induced developmental toxicity using human embryonic stem cells. Cell Biol Int. Nov. 2008;32(11):1412-24. doi: 10.1016/j.cellbi.2008.08.012. Epub Aug. 20, 2008.
Paik et al., Rapid micropatterning of cell lines and human pluripotent stem cells on elastomeric membranes. Biotechnol Bioeng. Oct. 2012;109(10):2630-41. doi: 10.1002/bit.24529. Epub Apr. 24, 2012.
Seiler et al., The validated embryonic stem cell test to predict embryotoxicity in vitro. Nat Protoc. Jun. 16, 2011;6(7):961-78. doi: 10.1038/nprot.2011.348.
Adler et al., First steps in establishing a developmental toxicity test method based on human embryonic stem cells. Toxicol In Vitro. Feb. 2008;22(1):200-11. Epub Sep. 4, 2007.
Ishii et al., Effects of extracellular matrixes and growth factors on the hepatic differentiation of human embryonic stem cells. Am J Physiol Gastrointest Liver Physiol. Aug. 2008;295(2):G313-21. doi: 10.1152/ajpgi.00072.2008. Epub Jun. 5, 2008.
Peerani et al., Patterning Mouse and Human Embryonic Stem Cells Using Micro-contact Printing. Stem Cells in Regenerative Medicine. Julie Audet and William L Stanford (Eds). Humana Press. 2009. Chapter 2. pp. 21-33.
Toh et al., Spatially organized in vitro models instruct asymmetric stem cell differentiation. Integr Biol (Camb). Dec. 2011;3(12):1179-87. doi: 10.1039/c1ib00113b. Epub Oct. 26, 2011.

* cited by examiner

*Primary Examiner* — Thaian N Ton
(74) *Attorney, Agent, or Firm* — Wolf, Greenfield & Sacks, P.C.

(57) ABSTRACT

A method and system of in vitro developmental toxicity testing comprising the steps of micropatterning an extracellular matrix; growing embryonic stem cells on the micropatterned extracellular matrix in the presence of mesoendodermal induction and testing for change of the geometrical mesoendoderm structure in the presence or absence of a test compound wherein (1) a decrease in mesoendodermal differentiation and/or (2) a change in morphology of the geometrical mesoendoderm structure in the presence of the test compound compared to cells in the absence of the test compound indicates that the test compound is a developmental toxic agent.

17 Claims, 12 Drawing Sheets (a)

(b)

D

E Kymograph d2: Random cell migration
d3: Directed collective cell migration

METHOD AND SYSTEM FOR IN VITRO DEVELOPMENTAL TOXICITY TESTING

CROSS-REFERENCE TO RELATED APPLICATION

This application is a national stage filing under 35 U.S.C. § 371 of international application PCT/SG2013/000426, filed Sep. 30, 2013, and claims the benefit of Singapore Patent Application No. 201207242-7 filed on Sep. 28, 2012, the entire contents of each of which are incorporated herein by reference.

FIELD OF THE INVENTION

The invention relates to a method and system for developmental toxicity testing.

BACKGROUND

The following discussion of the background to the invention is intended to facilitate an understanding of the present invention. However, it should be appreciated that the discussion is not an acknowledgment or admission that any of the material referred to was published, known or part of the common general knowledge in any jurisdiction as at the priority date of the application.

Birth defects are one of the leading causes of infant mortality worldwide[1,2,3] and can also result in long-term disabilities and illnesses. Abnormalities during fetal development can be due to either genetic conditions or environmental exposure during pregnancy, especially the first trimester. Therefore, regulatory bodies, such as the US Environmental Protection Agency (EPA), have mandated that environmental agents, such as drugs, chemicals and pesticides should be evaluated for developmental toxicity[4].

Testing developmental toxicity on animals is limited by cost and ethical issues. Hence, a number of alternative animal embryo or cell-based in vitro developmental models have been developed, which include the frog embryo teratogenesis assay (FETAX)[5], the chicken embryo toxicity screening test (CHEST)[6], the micromass (MM) assay using mouse embryonic mesenchymal cells[7], the mouse or rat whole embryo culture (WEC) assay[8], the zebrafish embryo-larva developmental toxicity assay[9], and the mouse embryonic stem cell test (EST)[10].

According to the European Centre for the Validation of Alternative Methods (ECVAM), only the MM assay, WEC and mouse EST for embryotoxicity testing are scientifically validated and can be considered for regulatory acceptance and application[11-13]. However, there are inter-species variations that cannot adequately explain differences in the molecular regulation of embryonic development between human and animals, or when used in reproductive toxicity testing, generate false negatives with devastating consequences. For instance, the withdrawn drug, Thalidomide, causes developmental deformation in human but not in mouse[14]. This technology aims to provide a human cell-based developmental model for research and screening applications in developmental toxicity.

There have been attempts to replace mouse ESCs used in the EST assay with human embryonic stem cells (hESCs)[16,17], although there have been no successful development of a human EST. The core standard of mouse EST is to evaluate the toxicity of compounds based on their effect on mouse embryonic stem cell (mESC) differentiation to beating cardiomyocytes[10]. By using mouse ES cell line D3 and mouse embryonic fibroblast cell line 3T3, they try to measure inhibition of cytotoxicity ($IC_{50}$) values for both cell lines, and inhibition of differentiation ($ID_{50}$) values for mESCs. They further classify the drug compounds into three classes as "non-embryotoxic", "weakly embryotoxic" and "strongly embryotoxic" using validated prediction model. The entire process lasts for 10 days using traditional beating cardiomyocytes monitoring under microscope or 7 days using FACS to check the gene expression of cardiac tissue. One major reason is that hESCs differentiate in vitro into cardiomyocytes at a slower rate and take longer time than mESCs (10-25% after 30 days)[18], making it impossible to count the beating cardiomyocytes on Day 10. Using RT-PCR or immunostaining method, researchers could acquire the data describing the effects of developmental toxins. However, lacking suitable scoring system makes it still unsatisfactory for drug testing application.

In 2010, Cezar's group showed for the first time the successful classification of drugs into developmental toxins and non-developmental toxins using metabolomics and random forest modeling[19]. However, they just tested those drugs in hESC pluripotency maintenance medium (i.e., mTeSR1 medium) instead of actually differentiating hESC, and they cannot further classify those developmental toxins into weak or strong developmental toxic compounds since only circulating concentration of the drugs was applied in the experiments.

While the current cell-based MM and EST assays can potentially incorporate human embryonic or pluripotent cells, the developmental process (i.e. cells differentiating into the 3 germ layers) is spontaneous, and disorganized in these models. Consequently, they do not provide a sensitive and reliable way of classifying developmental toxins, which includes embryo toxins and teratogens, because the assays are either measuring general cytotoxicity[7] or inhibition of cardiac tissue formation[10], and are too crude to capture an important aspect of developmental toxicity—disruption of differentiation patterns. Current EST models rely on measuring inhibition of cardiomyocyte formation by xenobiotics as an indicator of developmental toxicity. Therefore it is not compatible with the intrinsic property of hESCs as hESCs do not form cardiomyocytes readily, unlike mouse ES cells.

The object of the invention is to ameliorate at least one of the problems mentioned herein.

SUMMARY OF THE INVENTION

Throughout this document, unless otherwise indicated to the contrary, the terms "comprising", "consisting of", and the like, are to be construed as non-exhaustive, or in other words, as meaning "including, but not limited to".

The present technology includes an in vitro method of developmental toxicity testing comprising the steps of:
 a. micropatterning an extracellular matrix;
 b. growing embryonic stem cells on the micropatterned extracellular matrix in the presence of a mesoendodermal induction medium for forming a geometrical mesoendoderm structure; and
 c. testing for change of the geometrical mesoendoderm structure in a presence or an absence of a test compound wherein (1) a decrease in mesoendodermal cell differentiation and/or (2) a change in morphology of the geometrical mesoendoderm structure in the presence of the test compound compared to cells in the absence of the test compound indicates that the test compound is a developmental toxic agent.

The use of a mesoendodermal induction agent mimics one of the earliest processes of embryonic development (primitive streak formation). The advantage of the method may be to have more than one quantitative descriptors of developmental toxic effects.

Other aspects and advantages of the invention will become apparent to those skilled in the art from a review of the ensuing description, which proceeds with reference to the following illustrative drawings of preferred embodiments.

BRIEF DESCRIPTION OF THE DRAWINGS

Preferred embodiments of the invention will be described, by way of illustrative examples only, with reference to the following drawings, of which.

DETAILED DESCRIPTION

Figure 1:
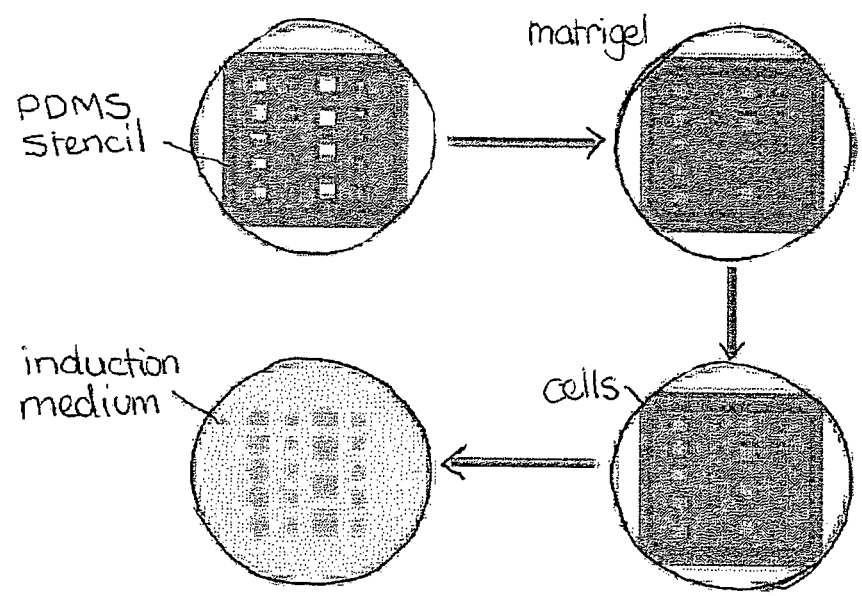
FIG. 1: Cell patterning using polydimethylsiloxane (PDMS) stencil.

An in vitro method of developmental toxicity testing is described comprising the steps of
micropatterning an extracellular matrix;
growing embryonic stem cells on the micropatterned extracellular matrix in the presence of a mesoendodermal induction medium for forming a geometrical mesoendoderm structure; and
testing for change of the geometrical mesoendoderm structure in the presence or absence of a test compound wherein (1) a decrease in mesoendodermal cell differentiation and/or (2) a change in morphology of the geometrical mesoendoderm structure in the presence of the test compound compared to cells in the absence of the test compound indicates that the test compound is a developmental toxic agent.

Preferably, the change in morphology of the geometrical mesoendoderm structure comprises a change in shape and/or location of the geometrical mesoendoderm structure.

Preferably, the mesoendodermal induction medium comprises a mixture of activin amino acid, bone morphogenic protein, and fibroblast growth factor 2. However, any medium known in the art to initiate mesoendodermal differentiation would be suitable. The mixture may further comprises vascular endothelial growth factor.

Activin may be any isolated, regenerative or synthetic activin protein known in the art. In mammals, four beta subunits of activin have been described, called activin $\beta_A$, activin $\beta_B$, activin $\beta_C$ and activin $\beta_E$. Preferably, activin A comprising a dimer of activin $\beta_A$ is used in the mesoendodermal induction medium. Preferably activin beta A chain has an amino acid sequence of SEQ ID NO. 1:

MPLLWLRGFLLASCWIIVRSSPTPGSEGHSAAPDCPSCALAALPKDVPNS

QPEMVEAVKKHILNMLHLKKRPDVTQPVPKAALLNAIRKLHVGKVGENGY

VEIEDDIGRRAEMNELMEQTSEIITFAESGTARKTLHFEISKEGSDLSVV

ERAEVWLFLKVPKANRTRTKVTIRLFQQQKHPQGSLDTGEEAEEVGLKGE

RSELLLSEKVVDARKSTWHVFPVSSSIQRLLDQGKSSLDVRIACEQCQES

GASLVLLGKKKKKEEEGEGKKKGGGEGGAGADEEKEQSHRPFLMLQARQS

EDHPHRRRRRGLECDGKVNICCKKQFFVSFKDIGWNDWIIAPSGYHANYC

EGECPSHIAGTSGSSLSFHSTVINHYRMRGHSPFANLKSCCVPTKLRPMS

MLYYDDGQNIIKKDIQNMIVEECGCS

Bone morphogenic proteins (BMP) are a group of growth factors also known as cytokines or as metabologens. There are twenty known BMPs. Any isolated regenerative or synthetic BMP may be suitable. Preferably BMP4 is used in the mesoendodermal induction medium. Preferably, human BMP4 has an amino acid sequence of SEQ ID NO. 2:

MIPGNRMLMVVLLCQVLLGGASHASLIPETGKKKVAEIQGHAGGRRSGQS

HELLRDFEATLLQMFGLRRRPQPSKSAVIPDYMRDLYRLQSGEEEEEQIH

STGLEYPERPASRANTVRSFHHEEHLENIPGTSENSAFRFLFNLSSIPEN

EVISSAELRLFREQVDQGPDWERGFHRINIYEVMKPPAEVVPGHLITRLL

DTRLVHHNVIRWETFDVSPAVLRWTREKQPNYGLAIEVTHLHQTRTHQGQ

HVRISRSLPQGSGNWAQLRPLLVTFGHDGRGHALTRRRRAKRSPKHHSQR

ARKKNKNCRRHSLYVDFSDVGWNDWIVAPPGYQAFYCHGDCPFPLADHLN

STNHAIVQTLVNSVNSSIPKACCVPTELSAISMLYLDEYDKVVLKNYQEM

VVEGCGCR

Fibroblast growth factors (FGF) are a group of growth factors. There are 22 known FGFs in humans which are all structurally related but only those FGFs that bind heparin, for example FGF2 would be suitable for use in the mesoendodermal induction medium. Preferably, human FGF2 has an amino acid sequence of SEQ ID NO. 3:

MVGVGGGDVEDVTPRPGGCQISGRGARGCNGIPGAAAWEAALPRRRPRRH

PSVNPRSRAAGSPRTRGRRTEERPSGSRLGDRGRGRALPGGRLGGRGRGR

APERVGGRGRGRGTAAPRAAPAARGSRPGPAGTMAAGSITTLPALPEDGG

SGAFPPGHFKDPKRLYCKNGGFFLRIHPDGRVDGVREKSDPHIKLQLQAE

ERGWSIKGVCANRYLAMKEDGRLLASKCVTDECFFFERLESNNYNTYRSR

KYTSWYVALKRTGQYKLGSKTGPGQKAILFLPMSAKS

In one embodiment the mesoendodermal induction medium further comprises vascular endothelial growth factor (VEGF). Vascular endothelial growth factor (VEGF) is a signal protein produced by cells that stimulates vasculogenesis and angiogenesis. The broad term 'VEGF' covers a number of proteins known in the art. VEGF may be used in the mesoendodermal induction medium. Preferably, human VEGF has an amino acid sequence of SEQ ID NO. 4:

MNFLLSWVHWSLALLLYLHHAKWSQAAPMAEGGGQNHHEVVKFMDVYQRS

YCHPIETLVDIFQEYPDEIEYIFKPSCVPLMRCGGCCNDEGLECVPTEES

NITMQIMRIKPHQGQHIGEMSFLQHNKCECRPKKDRARQEKKSVRGKGKG

QKRKRKKSRYKSWSVYVGARCCLMPWSLPGPHPCGPCSERRKHLFVQDPQ

TCKCSCKNTDSRCKARQLELNERTCRCDKPRR

In one embodiment the micropatterning is achieved by fabricating a stencil of a polydimethylsiloxane (PDMS) sheet having a plurality of geometric shapes cut into the PDMS sheet the PDMS stencil is sealed into a culture container, the matrix is coated over the PDMS stencil within the culture container such that when the PDMS stencil is removed only cells growing in the plurality of geometric shapes remain in the culture container. Preferably, the culture container is a petri dish or a well in a 96 well plate, however any container that will hold a matrix to grow embryonic stem cells would be suitable.

In another embodiment the micropattern is formed by applying a plurality of growth factor gradients on the matrix. The plurality of growth factor gradients may be printed onto the matrix as a plurality of geometric shapes using methods such as microcontact printing, microfluidic patterning, inkjet printing or any other method known in the art to print a pattern onto a matrix.

In a one embodiment the plurality of geometric shapes are all the same size and shape.

In another embodiment the plurality of geometric shapes vary in size or vary in shape.

The plurality of geometric shapes may be any shape for example circular, square, semi-circular, rectangular or any shape required.

Preferably the culture media comprises a gelatinous protein mixture secreted by Engelbreth-Holm-Swarm (EHS) mouse sarcoma cells. This is known as Matrigel™ (BD Biosciences) or Cultrex BME™ (Trevigen Inc). Other suitable culture mediums able to support embryonic cell growth and differentiation would be suitable such as gelatin, laminin or synthetic peptides known in the art.

The method of testing can be used with any embryonic stem cells but preferably the embryonic stem cells are human embryonic stem cells (hESC). In one embodiment the embryonic stem cells are seeded at a density of 4 million cells/ml.

Preferably the testing for mesoendodermal cell differentiation is achieved by incubating the cells with antibody against a mesoendodermal marker and imaging the cells for detection of the marker.

Preferably a variation in mesoendodermal cell differentiation at an outer perimeter of the micropattern in the presence of the test compound compared to in the absence of the test compound indicates that the test compound is a developmental toxic agent.

Our proposed technology provides a novel approach of assessing for chemical- or drug-induced developmental toxicity in human stem cells. Our technology recapitulates spatial patterning of mesoendoderm differentiation, which marks the earliest differentiation event in a localized region of a gastrulating embryo. We achieve this by patterning human stem cells onto extracellular matrix (ECM) islands of specified geometries to impose a mechanical gradient on the human embryonic stem cell (hESC) colony. Cells at the geometry edge of the colony are predisposed to differentiate into mesoendoderm. The micropatterned hESC colonies can generate mesoendoderm patterns corresponding to the geometrical shape of the colony. This differentiation pattern can be disrupted by known teratogens, such as valproic acid and thalidomide, at non-cytotoxic concentrations. The differentiation pattern arising from the endogenous mechanical stress in the micropatterned human stem colony can be quantified via image processing, and provides a quantitative measurement for the developmental toxicity of different chemicals and drugs.

Spatially patterned hESC differentiation arising from endogenous mechanical gradient in micropatterned cell colony.

Our technology can complement ToxCast, which uses computational modeling to predict liver and developmental toxicity, by providing hESC experimental data to refine the v-Embryo database.

The micropatterned platform can be used as an experimental tool for studying developmental biology.

The advantages of our technology includes the following:—
- Technique works with human embryonic or pluripotent stem cells
- Our proposed technique has been shown to work with human ES cells.
- Shorter time to establish model for experimentation/drug testing.
- 3 days instead of 7/10 days in mouse EST.
- Measures disruption of differentiation pattern instead of changes in level of differentiation, which is difficult to benchmark.
- By measuring disruption of differentiation pattern, we can quantitatively acquire of the Asymmetrical Ratio change, based on which a clear classification of the drugs could be made. However, in current models which measure changes in the level of differentiation of hESC, since even the expression changes of different genes that belong to the same lineage can be quite different from one another under the same conditions.
- Discriminates between non-specific cytotoxicity and disruption of lineage-specified differentiation.
- Our technology generates hESC differentiation patterns and measures disruption of these morphological patterns as the assay read-out for developmental toxicity testing. Since we do not measure cell viability, our measurement is not confounded with general cytotoxicity, which also affects cell viability.
- Compatible with high-throughput and high-content image analysis systems.
- For example, we can adapt our model to a 96-well plate format, which could make matrix coating much easier and less time-consuming. After seeding hESC in the 96-well plate, all the following sample preparation procedures including daily medium change and immunofluorescence staining could be automated using a JANUS™ automated liquid handling system (Perkin Elmer) (customized by BioLaboratories, Singapore). Furthermore, images could be acquired using Cellomics® ArrayScan® VTI HCS Reader (Thermo Scientific) to significantly improve imaging speed. Finally, for data analysis, we could just modify the program to make it capable of doing serial Asymmetrical Ratio calculations in MATLAB software.

Instead of controlling spatial differentiation using mechanical stress, we can also directly pattern growth factors to induce localized differentiations, forming a growth factor gradient rather than a sparcial gradient which may also be applicable for developmental toxicity testing. In this example the micropatterning is made by varying the amount of mesoendodermal induction medium on a culture medium. Growth factor patterning using multi-step micropatterning or microfluidics, may be more difficult to handle but would still work.

EXAMPLE

Materials & Methods

Cell Patterning

In order to generate gradients of mechanical stress, circle or square shapes of Matrigel matrix with two different sizes (785000 µm2 or 196250 µm2) were designed using AutoCAD software. Then polydimethylsiloxane (PDMS) stencils were fabricated by using a laser-cutter (Universal Laser System) to cut the designated shape patterns on a 127 µm thick PDMS sheet (Specialty Silicone Products Inc.) and then bonding it to a laser-cut, 2 mm thick PDMS gasket. For cell patterning, the PDMS stencil was first sealed into a 60 mm petri dish by adding 200 µl 70% ethanol and dried in the tissue culture hood, then Matrigel™ (BD Biosciences) matrix was coated by at least hour incubation with the Matrigel™ solution (FIG. 1). Thereafter cells were seeded at a density of 4 million cells/ml. After 1 hour incubation for cell attachment, the stencil and excess unattached cells were removed. The surface was then passivated with 0.5% pluronic acid for 10 mins before 3-time washing. The acquired patterned hESC were incubated overnight in mTesR1 maintenance medium (StemCell Technologies) for stabilization and the mesoendoderm induction was started the next day.

Mesoendoderm Induction

The differentiation of patterned hESC colonies were induced by mesoendoderm induction medium, which comprises of 100 ng/ml Activin, 25 ng/ml BMP4 and 10 ng/ml FGF2 in basal serum-free APEL™ medium (STEMdiff™, StemCell Technologies). For developmental toxicity testing, the patterned hESC colonies were cultured in mesoendoderm induction medium together with the test chemical. The induction lasted 3 days and the medium is half changed daily with/without the test chemical.

Immunofluorescence Staining, Imaging & Data Analysis

Figure 5:
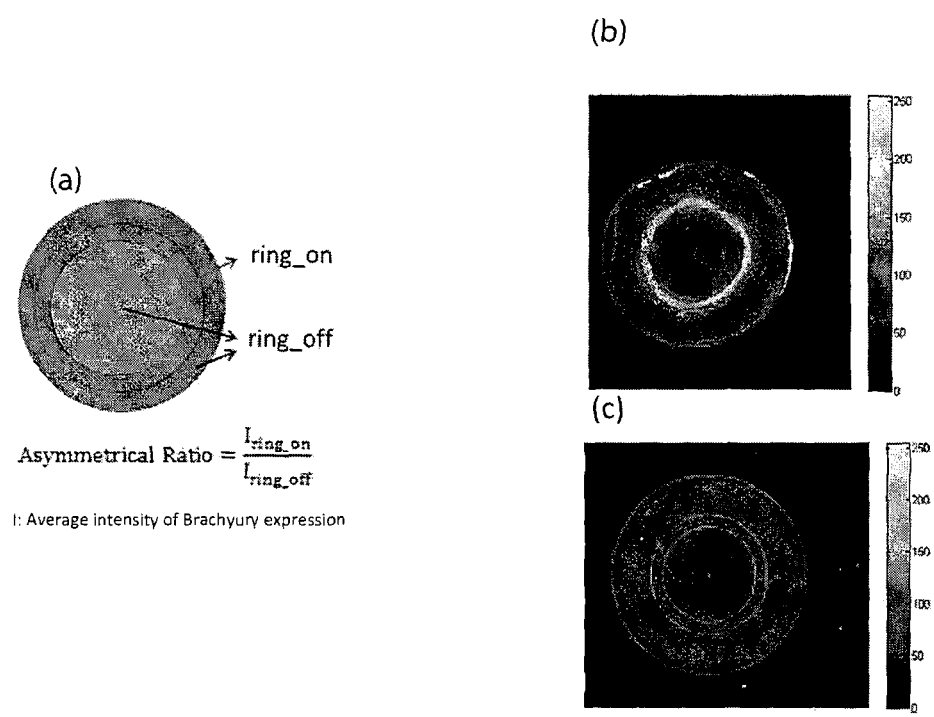
FIG. 5: Asymmetrical Ratio Calculation. First acquire the radii of the ring (red color in a) & b)) using untreated hESC colonies, then apply this ring as a mask to hESC colonies treated with teratogens (c), calculate the two kinds of Asymmetrical Ratios independently and compare the relative change.

Samples were fixed on Day 3 of differentiation. Immunofluorescence staining was done to check the expression distribution of early mesoendodermal marker Brachyury. Image acquisition was done under 10× objective using Olympus fluorescence microscope and Asymmetrical Ratio was calculated using MATLAB programming (FIG. 5).

Results

Spatial Asymmetrical Mesoendormal Differentiation Pattern Formed In Vitro

Figure 2:
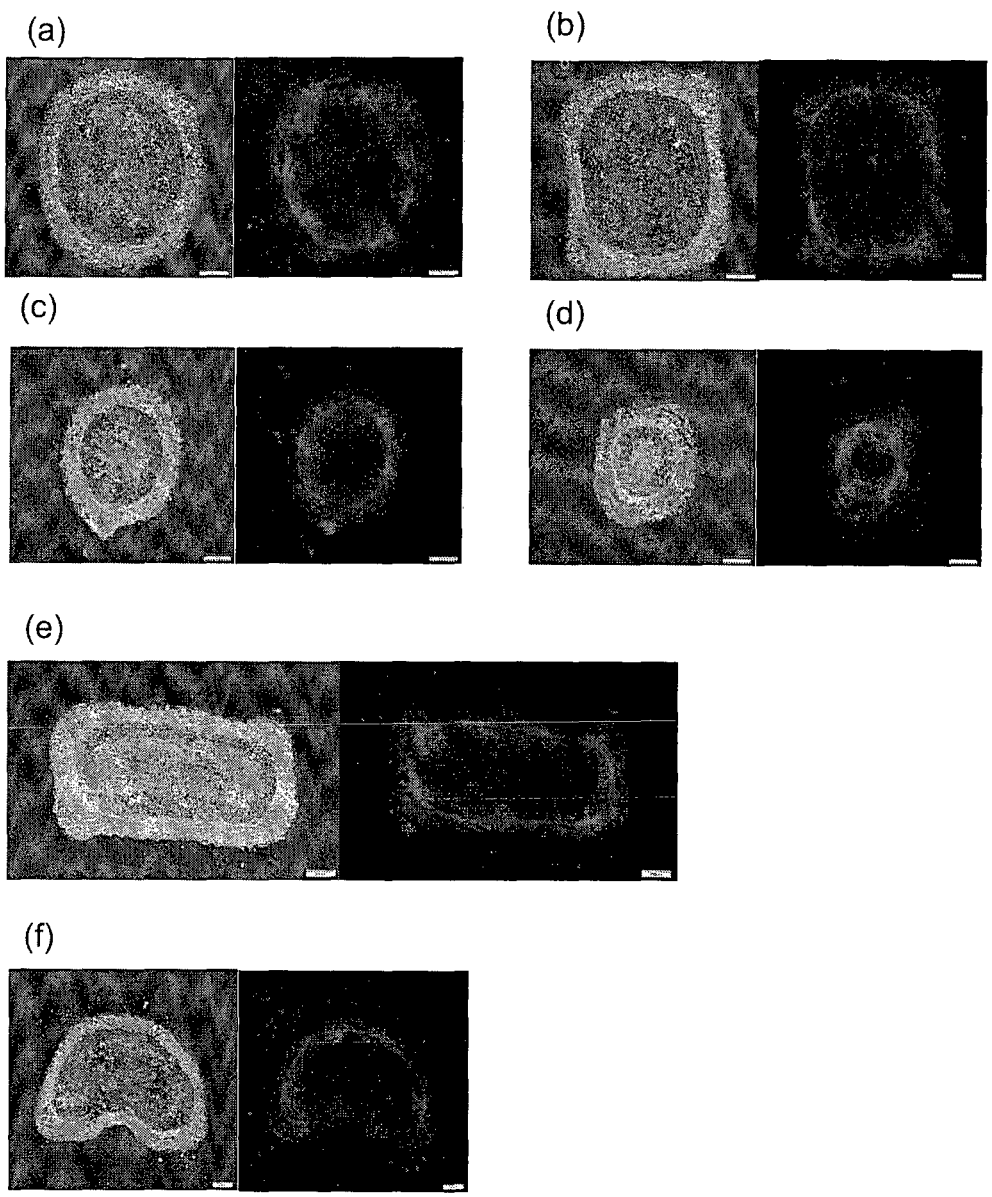
FIG. 2: Formation of a geometrical mesoendoderm structure coinciding with the shape of the hESC colonies after 3 days of differentiation. (a), (b), (e), (f) are hESC colonies with the area of 785000 μm²; (c), (d) are hESC colonies with the area of 196250 μm². Red: Immunofluorescence staining for mesoendodermal marker Brachyury; Scale bar: 200 μm.
Figure 3:
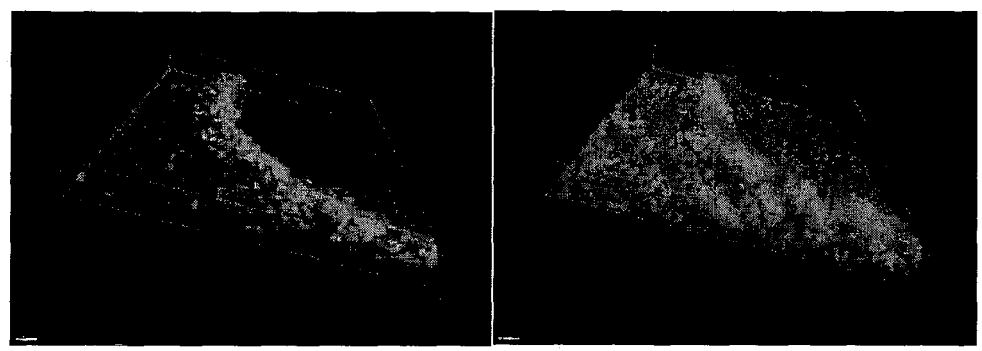
FIG. 3: Confocal scans of the edge of hESC colony (circle). Red: Brachyury, Blue: DAPI. (a) 3-D reconstruction shows that Brachyury-positive cells localize at the edges of hESC colony, forming a shining "ring"; (b) Z-stack shows that Brachyury-positive cells only localize on the top layer of the cell sheet, and there is a "tube-like" structure beneath the shining "ring". Scale bar: 30 μm.
Figure 3:
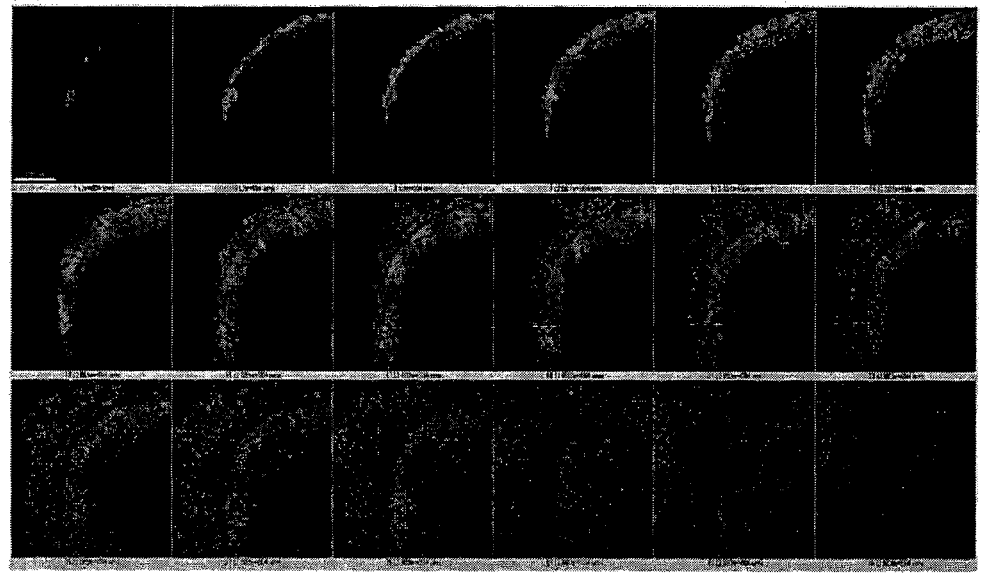

After 3 days of culture in mesoendoderm induction medium, the spatial localization of mesoendoderm in the colonies were coincidental with the geometrical shapes of the colonies, forming a "ring-like" structure (FIG. 2 & FIG. 3). In other words, after 3 days of differentiation, there is formation of a geometrical mesoendoderm structure coinciding with the shape of the hESC colonies. This "ring-like" structure had a unique 3-D structure, with Brachyury-positive cells sitting on the top layer of the cell sheet, and a "tube-like" structure forming beneath the shining "ring". This phenomenon indicated that localized cell differentiation and morphogenetic movements did occur in our system, which are also concurrent and inevitable in human embryogenesis.

Spatial Asymmetrical Pattern Disruption by Teratogens

Figure 4:
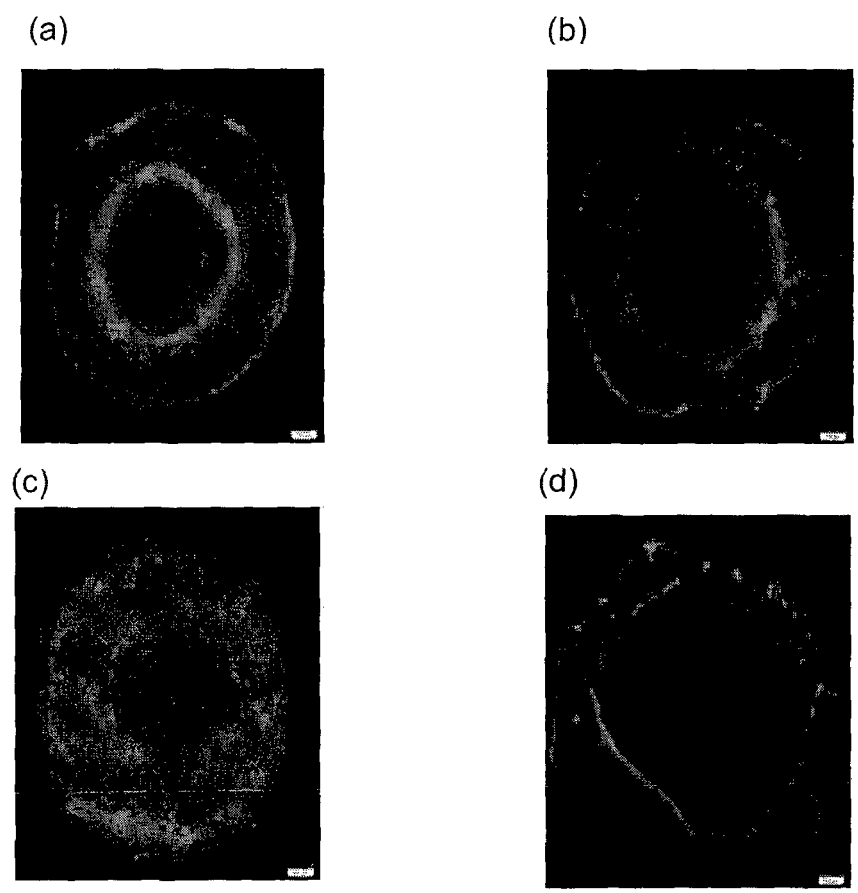
FIG. 4: The expression of Brachyury with/without drug treatment after 3 days of differentiation. T expression was mis-localized after treated with 5-fluorouracil (5-FU) (b), valproic acid (VPA) (c) or Thalidomide (d). Scale bar: 100 μm.
Figure 6:
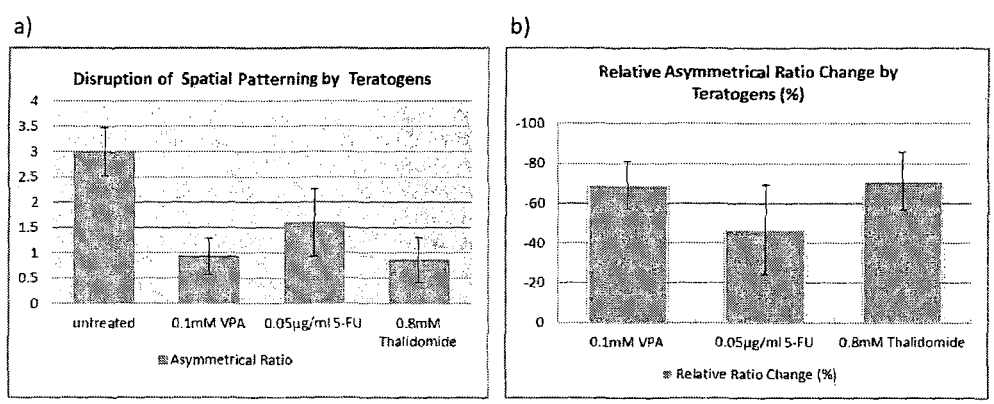
FIG. 6: Teratogen-induced change in Asymmetry Ratio relative to untreated control. a) Asymmetrical Ratio value with or without teratogen treatment. b) The relative Asymmetrical Ratio change after teratogen treatment compared with untreated control. For 0.05 μg/ml 5-FU, the Asymmetrical Ratio decreased by 46.7%, from 3 to 1.6; for 0.1 mM VPA and 0.8 mM Thalidomide, the Asymmetrical Ratio decreased by ~70%, from 3 to ~0.9

Three known teratogens (0.1 mM Valproic acid (VPA), 0.05 ug/ml 5-Fluorouracil (5-FU), and 0.8 mM Thalidomide) were tested using this model. Mesoendoderm induction medium together with the drug was added into our model and incubated for 3 days before the samples were fixed for immunofluorescence staining of Brachyury. Half of the medium was changed daily with the drug. An untreated control which was only cultured in mesoendoderm induction medium without any drug was also done. Results showed that all of the three drugs could disrupt the original asymmetrical differentiation pattern, i.e. destroy the "ring" formation (FIG. 4). In order to measure the disruption, we used Asymmetrical Ratio as a parameter to evaluate the asymmetrical patterns with or without drug treatment, which indicate the average intensity ratio of "ring" area to "off-ring" area (FIG. 5). Results showed that for untreated controls, the average Asymmetrical Ratio was around 2.5-3.5 (FIG. 6). When treated with teratogens, Asymmetrical Ratio values were significantly decreased by developmental toxicity effects. For 0.05 μg/ml 5-FU, the Asymmetrical Ratio was decreased by 46.7%, from 3 to 1.6; and for 0.1 mM VPA and 0.8 mM Thalidomide, the Asymmetrical Ratio was decreased by ~70%, from 3 to ~0.9. These results implied that our model was quite sensitive to different teratogen treatments (FIG. 6), the effects of which could be quantitatively measured and used for drug classification and scoring.

Geometrical Shaped Stencil

Stencils of different geometrical shapes (rectangle, circle, semi-circle, square) were made to determine if PS induction was affected with H9 hESCs 1. 60 mm PS dish was used,
2. The stencil was sealed onto the 60 mm PS dish with ethanol,
3. It was dried under UV light 2 plates were made Plate 1: had a mixture of large and small shapes
Plate 2: had large sized shapes only 1. Warm mTeSR 1, accutase and DMEM/F12
2. Supplement 3 ml TeSR1 with 10 um ROCKi (add 2 ul of 5 mM stock per medium).
3. Remove differential regions,
4. Wash culture once with DMEM/F12,
5. Add 1 ml of accutase per 60 mm dish and incubate at 37° C. for 5-10 min,
6. Triturate gently to break colonies into single cells
7. Transfer cells into 15 ml tube,
8. Rinse plate with at least 5 ml of DMEM/F12 per 1 ml of accutase and collect medium into the 15 ml tube,
9. Centrifuge cells at 1000 rpm, 3-5 min,
10. Remove cells and resuspend in 1.5 ml of supplemented mTeSR1 per stencil (use 3×6 wells for 2× stencils),
11. Aspirate cell suspension, wash once with DMEM/F12,
12. Add 3 ml of DMEM/F12 to area surrounding stencil. Use a foforcep to gently remove stencil. Remove DMEM/F12,
13. Add 3 ml of APEL medium+1 ng/ml Activin A, 25 ng/ml BMP4 and 10 ng/ml of FGF2,
14. Change half of volume after 2 days (1.5 ml),
15. Fix and perform immunostaining.

Immunostaining

Samples were fixed for 20 min in 3.7% paraformaldehyde, and permeabilized for 15 min with 0.5% Triton X-100 in PBS. After overnight incubation at 4° C. in blocking buffer (2% BSA and 0.1% Triton X-100 in TBS buffer), they were incubated overnight at 4° C. with primary antibodies (5-10 μg/ml in blocking buffer). The primary antibody used was goat-anti-Brachyury (10 μg/ml, AF2085, R&D systems). The samples were washed 5 times with 15 min interval before adding the Alexa Fluor dye-conjugated secondary antibodies (1:1000, Molecular Probes). After 1 hr incubation at room temperature, samples were washed for 5 times with 15 min interval and counter-stained with Hoechst 33342 (10 μg/ml, Molecular Probes) for 5 min. After that, samples were washed 3 times with PBS and then mounted using Fluor-save™ (Calbiochem).

Figure 7:
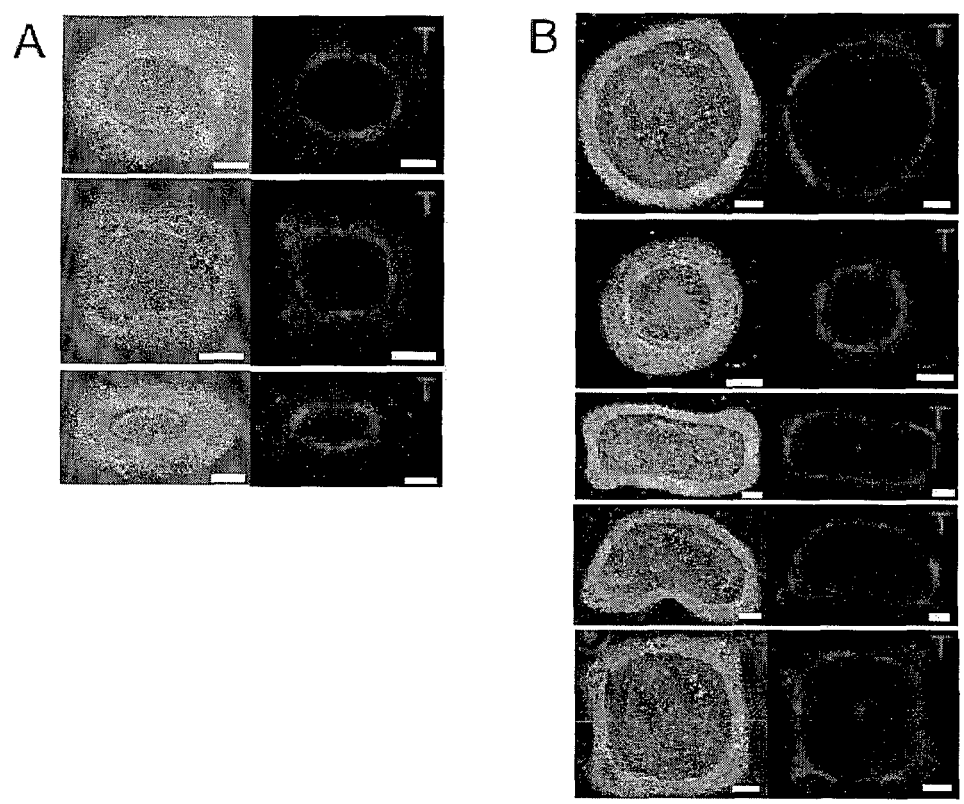
FIG. 7: Images of geometrical mesoendoderm structures formed from micropatterning different hESC cell lines. (A): Micropatterned H9 hESCs after 3 days of differentiation. (B): Micropatterned H1 hESCs after 3 days of differentiation

FIG. 7 shows images of geometrical mesoendoderm structures formed from micropatterning different hESC cell lines. Two hESC lines (H9 and H1) that were micropatterned into different shapes and sizes generated a geometrical mesoendoderm structure after 3 days of mesoendoderm differentiation. FIG. 7A shows micropatterned H9 hESCs after 3 days of differentiation and FIG. 7B shows micropatterned H1 hESCs after 3 days of differentiation. Left panel shows phase contrast images; right panel shows immunostaining of mesoendoderm marker, Brachury (T). Scale bars=200 μm.

Figure 8:
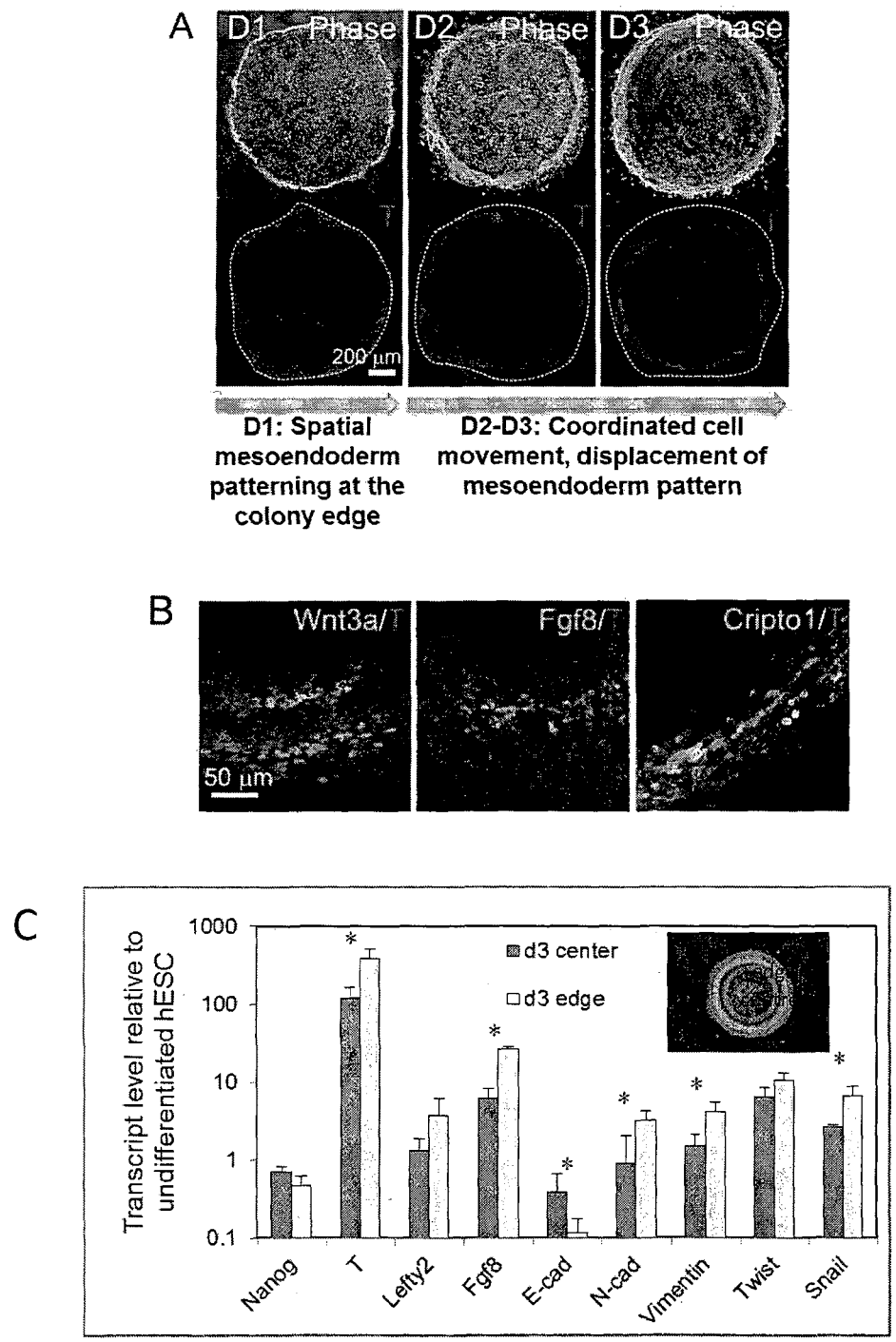
FIG. 8: The geometrical mesoendoderm structure was formed by spatially patterned differentiation followed by coordinated morphogenetic cell movement. (A): The phase and fluorescence images of the micropatterned hESC (μP-hESC) colony on day1-day3. The mesoendoderm (T⁺) cells were spatially patterned at the colony edge on day 1, then displaced to ~150-200 μm away from the colony edge on day 3. (B): Spatial patterning of other mesoendoderm markers after 3 days of differentiation. Wnt3a, Fgf8, Cripto1 (green) colocalized with T (red) in the μP-hESC colony. (C): Transcription levels of epithelial-mesochymal transition (EMT) markers around the μP-hESC colony edge and center. Cells near the edge of the μP-hESC colony have a higher expression levels of EMT markers such as Snail and Vimentin compared with cells in the colony centre: Brachyury (T), Wnt3a, Fgf8 and Cripto1 are all mesoendoderm markers. (D): The montage of the 3-day live imaging of the μP-hESC colony under 10× objective showed the movement of the cells during the 3-day differentiation. (E): Kymograph analysis along the yellow line of the colony on FIG. 1D during the 3-day live imaging window. Cells near the colony edge showed random cell migration on day 2, but underwent directed collective cell movement on day 3.
Figure 8:
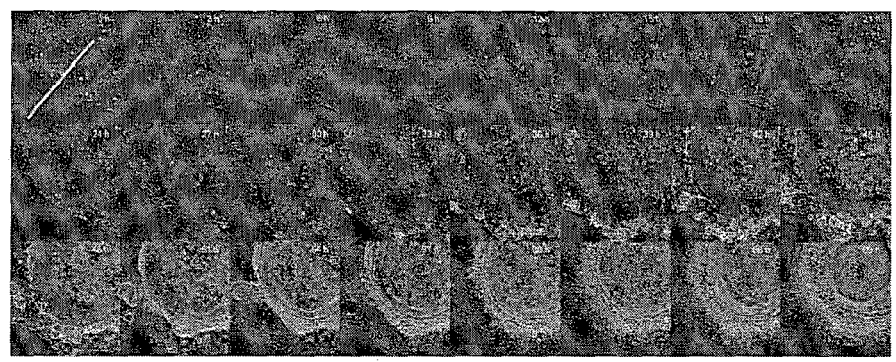
Figure 8:
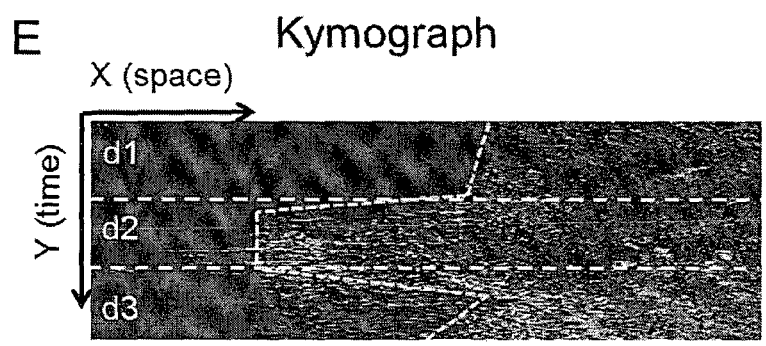

Spatially Patterned Differentiation Followed by Coordinated Morphogenetic Cell Movement FIG. 8 shows the characterization of the geometrical mesoendoderm structural motif. The geometrical mesoendoderm structure was formed by spatially patterned differentiation followed by coordinated morphogenetic cell movement. FIG. 8A shows the phase and fluorescence images of the micropatterned hESC (μP-hESC) colony on day1-day3 (D1-D3). The mesoendoderm (T$^+$) cells were spatially patterned at the colony edge on day 1, then displaced to ~150-200 μm away from the colony edge on day 3. The geometrical structural motif is formed by (1) spatially patterned mesoendoderm differentiation followed by (2) coordinated cell movement (FIG. 8A).

FIG. 8B shows spatial patterning of other mesoendoderm markers after 3 days of differentiation; Wnt3a, Fgf8, Cripto1 (green) colocalized with T (red) in the μP-hESC colony. FIG. 8C shows transcription levels of epithelial-mesochymal transition (EMT) markers around the μP-hESC colony edge and center. Cells near the edge of the μP-hESC colony have higher expression levels of EMT markers such as Snail and Vimentin compared with cells in the colony centre. Brachaury (T), Wnt3a, Fgf8 and Cripto1 are all mesoendoderm markers. Spatially patterned differentiation was indicated by the localized expression of mesoendoderm markers, Bachyuary, Fgf8, Cripto1 and Wnt3a, (FIG. 8B); and epithelial-mesenchymal transition activity (FIG. 8C).

FIG. 8D shows the montage of the 3-day live imaging of the μP-hESC colony under 10× objective which showed the movement of the cells during the 3-day differentiation. FIG.

8E shows a kymograph analysis along the yellow line of the colony on FIG. 1D during the 3-day live imaging window. Cells near the colony edge showed random cell migration on day 2, but underwent directed collective cell movement on day 3. Spatially localized differentiated cells (at edge of stem cell colony) underwent coordinated cell movement to form a 3D-like structural motif as observed by live imaging (FIG. 8D). The trajectory of the coordinated cell movement can be seen from a space-time plot (kymograph) of the differentiating stem cells (FIG. 8E).

Figure 9:
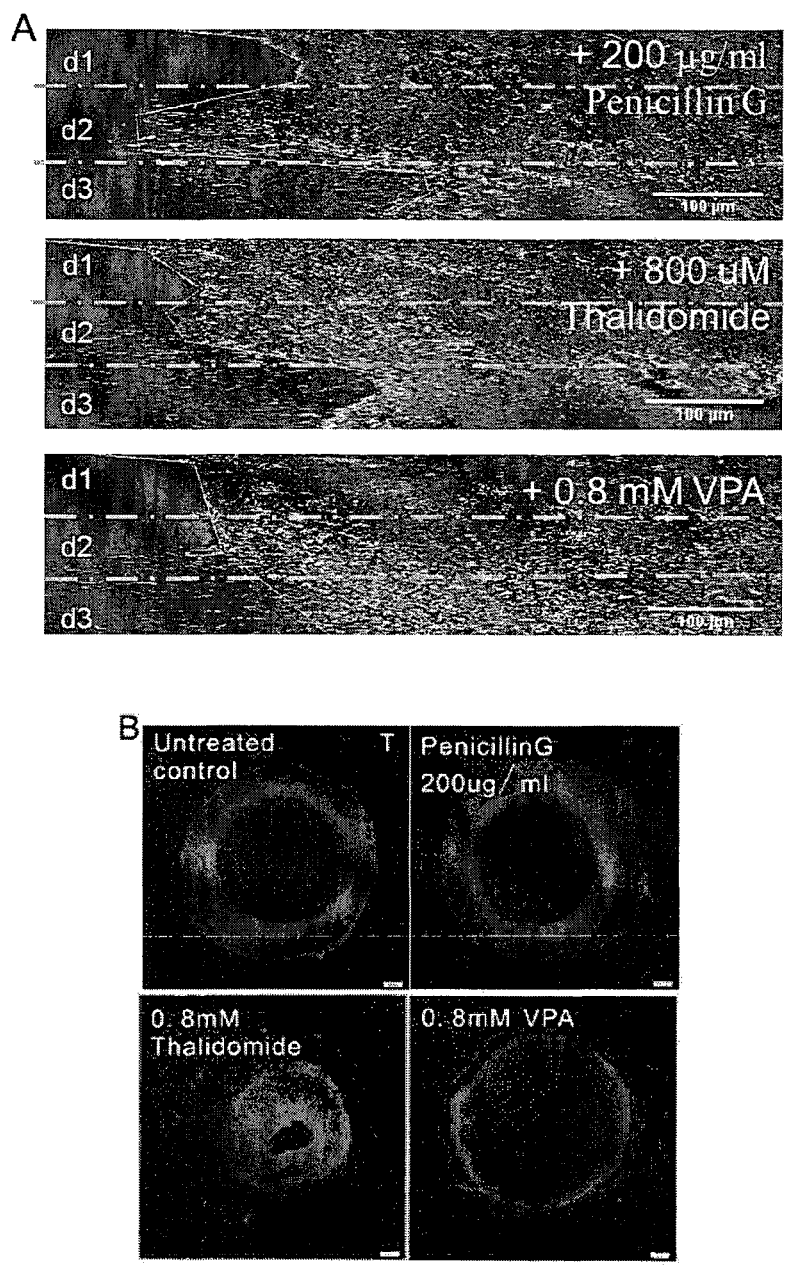
FIG. 9: Developmental toxic drugs affected the physical morphology/localization of the mesoendoderm structure in the μP-hESC model. (A): Kymographs of the μP-hESC colony under drug treatment. The trajectories of the collective cell migration under developmental toxic drug treatment (Thalidomide & VPA) were disrupted during day2-3, while the collective cell migration under non-developmental toxic drug treatment (Penicillin G) was unaffected. (B): Mesoendoderm marker T localization with/without drug treatment on day3. The localization of the mesoendoderm motif (T⁺ region) was misplaced when treated with Thalidomide or VPA, while remained unchanged when treated with negative control drug Penicillin G. Scale bar: 100 μm.

Developmental Toxic Drugs Affected Physical Morphology/Localization of Mesoendoderm Structure in μP-hESC Model FIG. 9 shows alterations to the geometrical mesoendoderm structural motif caused by known developmental toxins. FIG. 9A shows kymographs of the μP-hESC colony under drug treatment. The trajectories of the collective cell migration under developmental toxic drug treatment (Thalidomide & VPA) were disrupted during day2-3, while the collective cell migration under non-developmental toxic drug treatment (Penicillin G) was unaffected. In other words, known developmental toxins, valproic acid and thalidomide, altered the trajectory of cell movement, whereas a non-developmental toxin (Penicillin G) did not (FIG. 9A). FIG. 9B shows Mesoendoderm marker T localization with/without drug treatment on day3. The localization of the mesoendoderm motif ($T^+$ region) was misplaced when treated with Thalidomide or VPA, while remained unchanged when treated with negative control drug Penicillin G. Scale bar: 100 μm. In other words, valproic acid and thalidomide also changes the morphology of the mesoendoderm structural motif, whereas untreated sample or penicillin G-treated sample did not (FIG. 9B).

Figure 10:
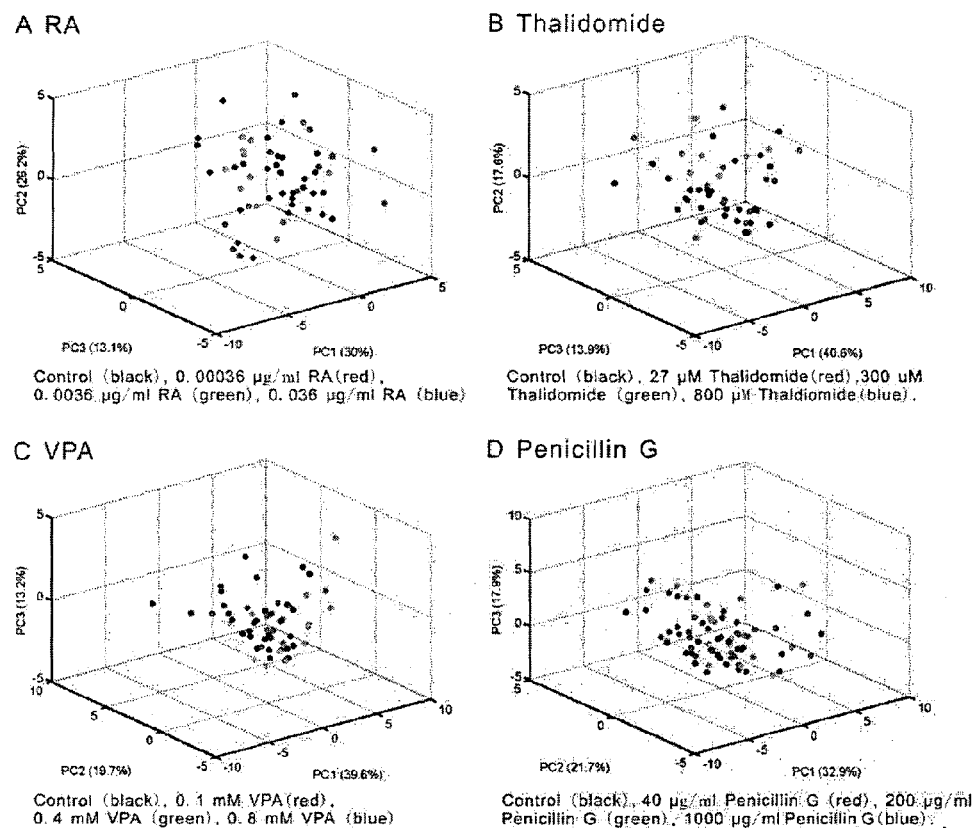
FIG. 10: PCA results of the dose-dependent developmental toxicity responses caused by developmental toxic drugs. (A-C): The spatial distribution of mesoendoderm motif within the μP-hESC colonies were significantly disrupted when treated with Retinoid acid (RA, >=0.0036 μg/ml), Thalidomide (>=300 μM), or VPA (>=0.8 mM). (D): The drug treatment of Penicillin G could not significantly disrupt the spatial distribution of the mesoendoderm motif within the μP-hESC colonies even when the concentration was 1000 μg/ml.

Dose-Dependent Developmental Toxicity Responses Caused by Developmental Toxic Drugs FIG. 10 shows that the proposed method is sensitive enough to detect different severity of drug-induced effects at different concentrations. Alterations to the different morphological features of the mesoendoderm structural motif were quantitatively measured by image processing at different concentrations of drugs. These morphological features at different drug concentrations were analyzed with principal component analysis (PCA). A data point represents each morphological feature; the data point color represents the drug concentration used in the treatment. FIG. 10A-C shows the spatial distribution of mesoendoderm motif within the μP-hESC colonies were significantly disrupted when treated with Retinoid acid (RA, >=0.0036 μg/ml), Thalidomide (>=300 μM), or VPA (>=0.8 mM). FIG. 10D shows the drug treatment of Penicillin G could not significantly disrupt the spatial distribution of the mesoendoderm motif within the μP-hESC colonies even when the concentration was 1000 μg/ml. For known developmental toxins i.e., (A) retinoic acid (RA), (B) thalidomide, (C) valproic acid (VPA), morphological features from the same drug concentration segregated into distinct clusters, and (D) For a non-developmental toxin (Penicillin G), morphological features from different drug concentration treatment cannot be segregated.

Data Collection Process:

1. Treat our μP-hESC colonies with 3 different concentrations of each drug and fix the samples on day 3 together with the untreated normal control samples. Acquire T immunofluorescence images of samples under Olympus fluorescence microscope.

2. Process all the T fluorescence images using Matlab to extract all the relevant morphological features of the samples representing the spatial distribution of the mesoendoderm motif ($T^+$ positive region in the images).

Primary Component Analysis (PCA):

Perform PCA in Matlab on all the extracted features across all the samples for each drug together with the untreated controls and plot the PCA results.

Drug Classification by their Developmental Toxicity Effects

Figure 11:
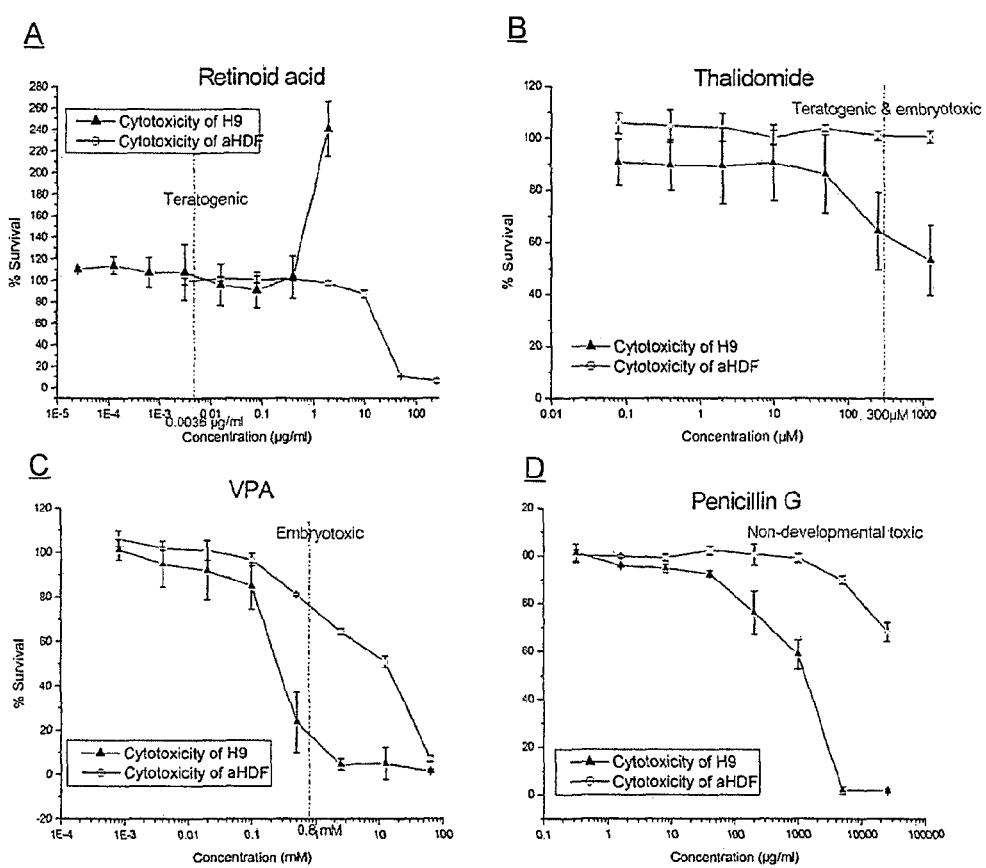
FIG. 11: Drug classification results based on PCA and cytotoxicity test (MTS) results. (A): The effective concentration (the lowest concentration of the drug which can significantly disrupted the spatial localization of the mesoendoderm motif in the μP-hESC models) of RA ($EC_{RA}$) was ~0.0036 μg/ml, which was not toxic either to hESC cell line H9 or to adult human dermal fibroblasts (aHDFs). Therefore RA is a developmental toxic drug which is teratogenic. (B): The $EC_{Thalidomide}$ was ~300 μM, which was not toxic to aHDFs but toxic to H9 cells (>50% survival). Therefore Thalidomide is a developmental toxic drug which is both teratogenic and embryotoxic. (C): The $EC_{VPA}$ was ~0.8 mM, which was a little toxic to aHDFs but very toxic to H9 cells (~20% survival). Therefore VPA is a developmental toxic drug which is very embryotoxic (which means very toxic to hESCs). (D): The $EC_{Penicillin\ G}$ was above 1000 μg/ml (which is the highest concentration tested for most developmental toxicity testing platforms). Therefore Penicillin G is a non-developmental toxic drug.

FIG. 11 shows that the proposed method can be combined with viability assays on adult and embryonic cells to correctly classify the drugs by their developmental toxicity effects. FIG. 11A shows the effective concentration (the lowest concentration of the drug which can significantly, disrupted the spatial localization of the mesoendoderm motif in the μP-hESC models) of RA ($EC_{RA}$) was ~0.0036 μg/ml, which was not toxic either to hESC cell line H9 or to adult human dermal fibroblasts (aHDFs). Teratogenic drugs alter morphology of mesoendoderm structural motif at concentrations that did not affect viability of both embryonic and adult cells (e.g., retinoic acid (FIG. 11A). Therefore RA is a developmental toxic drug which is teratogenic.

When the effective drug concentration resulting in alteration to the structural motif overlaps with the drug concentration reducing embryonic cell viability, the drug is embryotoxic (e.g. thalidomide and valproic acid (FIG. 11B-C)). FIG. 11B shows the $EC_{Thalidomide}$ was ~300 μM, which was not toxic to aHDFs but toxic to H9 cells (>50% survival). Therefore Thalidomide is a developmental toxic drug which is both teratogenic and embryotoxic. FIG. 11C shows the $EC_{VPA}$ was ~0.8 mM, which was a little toxic to aHDFs but very toxic to H9 cells (~20% survival). Therefore VPA is a developmental toxic drug which is very embryotoxic (which means very toxic to hESCs).

When the mesoendoderm structural motif was not affected at drug concentrations where one observes decrease in cell viability of adult and embryonic cells, the drug is non-developmental toxic (e.g. penicillin G (FIG. 11D)). FIG. 11D shows the $EC_{Penicillin\ G}$ was above 1000 μg/ml (which is the highest concentration tested for most developmental toxicity testing platforms). Therefore Penicillin G is a non-developmental toxic drug.

Those skilled in the art will appreciate that the invention described herein is susceptible to variations and modifications other than those specifically described. The invention includes all such variation and modifications. The invention also includes all of the steps, features, formulations and compounds referred to or indicated in the specification, individually or collectively and any and all combinations or any two or more of the steps or features.

Each document, reference, patent application or patent cited in this text is expressly incorporated herein in their entirety by reference, which means that it should be read and considered by the reader as part of this text. That the document, reference, patent application or patent cited in this text is not repeated in this text is merely for reasons of conciseness.

Any manufacturer's instructions, descriptions, product specifications, and product sheets for any products mentioned herein or in any document incorporated by reference herein, are hereby incorporated herein by reference, and may be employed in the practice of the invention.

The present invention is not to be limited in scope by any of the specific embodiments described herein. These embodiments are intended for the purpose of exemplification only. Functionally equivalent products, formulations and methods are clearly within the scope of the invention as described herein.

The invention described herein may include one or more range of values (e.g. size, concentration etc). A range of values will be understood to include all values within the range, including the values defining the range, and values adjacent to the range which lead to the same or substantially the same outcome as the values immediately adjacent to that value which defines the boundary to the range.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

REFERENCES

1. Petrini, J., Damus. K. and Johnston, R. B., Jr. An overview of infant mortality and birth defects in the United States. *Teratology* 56, 8-10 (1997).
2. Heron, M. et al. Deaths: Final data for 2006. Natl. Vital Stat. Rep. 57, 1-134 (2009).
3. Tan, K. H. et al. Birth defects in Singapore: 1994-2000. *Singapore Med. J.* 46, 545-552 (2005).
4. U.S. Environmental Protection Agency, E. Guidelines for Developmental Toxicity Risk Assessment. (1991).
5. Bantle, J. a., Fort, D J., Rayburn, J. R., DeYoung, D. J. and Bush, S. J. Further validation of FETAX: Evaluation of the developmental toxicity of five known mammalian teratogens and non-teratogens. *Drug. Chem. Toxicol.* 13. 267-282 (1990).
6. Jelinek, R., Peterka. M. and Rychter, Z. Chick embryotoxicity screening test—130 substances tested. *Indian J. Exp. Biol.* 23, 588-595 (1985).
7. Flint, O. P. In vitro tests for teratogens: Desirable endpoints, test batteries and current status of the micromass teratogen test. *Reprod. Toxicol.* 7 Suppl 1, 103-111 (1993).
8. Sadler, T. W., Horton, W. E. and Warner, C. W. Whole embryo culture: S screening technique for teratogens? *Teratog. Carcinog. Mutagen* 2, 243-253 (1982).
9. Hill, A. J. Zebrafish as a Model Vertebrate for Investigating Chemical Toxicity. *Toxicological Sciences* 86, 6-19 (2005).
10. Seiler, A. E. M. and Spielmann, H. The validated embryonic stem cell test to predict embryotoxicity in vitro. *Nature Protocols* 6, 961-978 (2011).
11. Balls, M. and Helisten, E. Statement on the scientific validity of the micromass test—An in Vitro for embryotoxicity. *Altem. Lab. Anim.*, 30, 268-270 (2002).
12. Balls, M. and Helisten, E. Statement on the scientific validity of the postimplantation rat whole-embryo culture assay—An in vitro test for embryotoxicity. *Altern. Lab. Anim.* 30, 271-273 (2002).
13. Balls, M. and Hellsten, E. Statement on the scientific validity of the embryonic stem cell test (EST)—An in Vitro test for embryotoxicity. *Altern. Lab. Anim.* 30, 265-268 (2002).
14. Knobloch, J., Shaughnessy, J. D., Jr. and Ruther, U. Thalidomide induces limb deformities by perturbing the Bmp/Dkkl/Wnt signaling pathway. *FASEB J.* 21, 1410-1421 (2007).
15. Gomez, E. W., Chen, Q. K., Gjorevski, N. and Nelson, C. M. Tissue geometry patterns epithelial-mesenchymal transition, via intercellular mechanotransduction. *J. of Cell. Biochem.* 110, 44-51 (2010).
16. Adler, S., Pellizzer, C., Hareng, L., Hartung, T. and Bremer, S. First steps in establishing a developmental toxicity test method based on human embryonic stem cells. *Toxicology in Vitro* 22, 200-211 (2008).
17. Mehta, A., Konala, V., Khanna, A. and Majumdar, A. Assessment of drug induced developmental toxicity using human embryonic stem cells. *Cell Biology international* 32, 1412-1424 (2008).
18. He, J. Q. Human embryonic stem cells develop into multiple types of cardiac myocytes: Action potential characterization. *Circulation Research* 93, 32-39 (2003).
19. West, P. R., Weir, A. M., Smith, A. M., Donley, E. L. R. and Cezar, G. G. Predicting human developmental toxicity of pharmaceuticals using human embryonic stem cells and metabolomics. *Toxicology and Applied Pharmacology* 247, 18-27 (2010).
20. Zhang, S. et al. A robust high-throughput sandwich cell-based drug screening platform. *Biomaterials* 32, 1229-1241 (2011).

The invention claimed is:

1. An in vitro method of testing developmental toxicity comprising the steps of:
   (a) differentiating a colony of pluripotent stem cells on a micropatterned extracellular matrix in the presence of a mesoendodermal induction medium and a test compound, wherein the differentiation of the colony coordinates cell movement and spatially patterned mesoendodermal differentiation and said differentiation forms a geometrical mesoendoderm structure in the colony; and
   (b) testing for a change in the spatially patterned differentiation of the geometrical mesoendoderm structure, wherein a disruption in the spatially patterned differentiation of the geometrical mesoendoderm structure compared to an untreated control colony of pluripotent stem cells indicates that the test compound is a developmentally toxic compound.

2. The method of claim 1, wherein the mesoendodermal induction medium comprises Activin, bone morphogenetic protein, and fibroblast growth factor.

3. The method of claim 2, wherein the mesoendodermal induction medium further comprises vascular endothelial growth factor.

4. The method of claim 1, wherein the disruption in spatial patterning of the geometrical mesoendoderm structure comprises a change in shape and/or location of the geometrical mesoendoderm structure.

5. The method of claim 1, further comprising micropatterning the extracellular matrix by fabricating a stencil of a polydimethylsiloxane (PDMS) sheet having geometric shapes cut into the PDMS sheet, sealing the PDMS stencil in a culture container, coating the extracellular matrix over the PDMS stencil within the culture container such that when the PDMS stencil is removed only cells growing in the geometric shapes remain in the culture container.

6. The method of claim 1, further comprising micropatterning the extracellular matrix by applying growth factor gradients on the extracellular matrix.

7. The method of claim 6, wherein the growth factor gradients are printed as geometric shapes onto the extracellular matrix.

8. The method of claim 5, wherein the geometric shapes are all the same size and shape, or the geometric shapes vary in size or shape.

9. The method of claim 5, wherein the geometric shapes are circular or square.

10. The method of claim 5, wherein the extracellular matrix comprises a gelatinous protein mixture secreted by Engelbreth-Holm-Swarm (EHS) mouse sarcoma cells.

11. The method of claim 1, wherein the pluripotent stem cells are human embryonic stem cells (hESCs).

12. The method of claim 1, wherein the pluripotent stem cells are seeded onto the extracellular matrix at a density of 4 million cells/ml.

13. The method of claim 1, wherein a disruption in the spatial patterning of the perimeter of the geometrical mesoendoderm structure indicates that the test compound is a developmentally toxic agent.

14. The method of claim 6, wherein the plurality of growth factor gradients are printed as geometric shapes onto the extracellular matrix, and wherein the geometric shapes are all the same size and shape, or the geometric shapes vary in size or shape.

15. The method of claim 6, wherein the growth factor gradients are printed as geometric shapes onto the extracellular matrix, and wherein the geometric shapes are circular or square.

16. The method of claim 6, wherein the growth factor gradients are printed as geometric shapes onto the extracellular matrix, and wherein the extracellular matrix comprises a gelatinous protein mixture secreted by Engelbreth-Holm-Swarm (EHS) mouse sarcoma cells.

17. The method of claim 1, wherein the testing step comprises extracting and quantifying at least one patterned feature of the geometrical mesoendoderm structure.

* * * * *

SEQUENCE LISTING

```
<160> NUMBER OF SEQ ID NOS: 4

<210> SEQ ID NO 1
<211> LENGTH: 426
<212> TYPE: PRT
<213> ORGANISM: Homo sapiens
<220> FEATURE:
<223> OTHER INFORMATION: Activin beta A chain

<400> SEQUENCE: 1

Met Pro Leu Leu Trp Leu Arg Gly Phe Leu Leu Ala Ser Cys Trp Ile
1               5                   10                  15

Ile Val Arg Ser Ser Pro Thr Pro Gly Ser Glu Gly His Ser Ala Ala
```

```
            20                  25                  30
Pro Asp Cys Pro Ser Cys Ala Leu Ala Ala Leu Pro Lys Asp Val Pro
            35                  40                  45
Asn Ser Gln Pro Glu Met Val Glu Ala Val Lys Lys His Ile Leu Asn
        50                  55                  60
Met Leu His Leu Lys Lys Arg Pro Asp Val Thr Gln Pro Val Pro Lys
65                  70                  75                  80
Ala Ala Leu Leu Asn Ala Ile Arg Lys Leu His Val Gly Lys Val Gly
                85                  90                  95
Glu Asn Gly Tyr Val Glu Ile Glu Asp Asp Ile Gly Arg Arg Ala Glu
            100                 105                 110
Met Asn Glu Leu Met Glu Gln Thr Ser Glu Ile Ile Thr Phe Ala Glu
            115                 120                 125
Ser Gly Thr Ala Arg Lys Thr Leu His Phe Glu Ile Ser Lys Glu Gly
        130                 135                 140
Ser Asp Leu Ser Val Val Glu Arg Ala Glu Val Trp Leu Phe Leu Lys
145                 150                 155                 160
Val Pro Lys Ala Asn Arg Thr Arg Thr Lys Val Thr Ile Arg Leu Phe
                165                 170                 175
Gln Gln Gln Lys His Pro Gln Gly Ser Leu Asp Thr Gly Glu Glu Ala
            180                 185                 190
Glu Glu Val Gly Leu Lys Gly Glu Arg Ser Glu Leu Leu Leu Ser Glu
            195                 200                 205
Lys Val Val Asp Ala Arg Lys Ser Thr Trp His Val Phe Pro Val Ser
        210                 215                 220
Ser Ser Ile Gln Arg Leu Leu Asp Gln Gly Lys Ser Ser Leu Asp Val
225                 230                 235                 240
Arg Ile Ala Cys Glu Gln Cys Gln Glu Ser Gly Ala Ser Leu Val Leu
                245                 250                 255
Leu Gly Lys Lys Lys Lys Glu Glu Glu Gly Glu Gly Lys Lys Lys
            260                 265                 270
Gly Gly Gly Glu Gly Gly Ala Gly Ala Asp Glu Glu Lys Glu Gln Ser
        275                 280                 285
His Arg Pro Phe Leu Met Leu Gln Ala Arg Gln Ser Glu Asp His Pro
290                 295                 300
His Arg Arg Arg Arg Gly Leu Glu Cys Asp Gly Lys Val Asn Ile
305                 310                 315                 320
Cys Cys Lys Lys Gln Phe Phe Val Ser Phe Lys Asp Ile Gly Trp Asn
                325                 330                 335
Asp Trp Ile Ile Ala Pro Ser Gly Tyr His Ala Asn Tyr Cys Glu Gly
            340                 345                 350
Glu Cys Pro Ser His Ile Ala Gly Thr Ser Gly Ser Ser Leu Ser Phe
        355                 360                 365
His Ser Thr Val Ile Asn His Tyr Arg Met Arg Gly His Ser Pro Phe
370                 375                 380
Ala Asn Leu Lys Ser Cys Cys Val Pro Thr Lys Leu Arg Pro Met Ser
385                 390                 395                 400
Met Leu Tyr Tyr Asp Asp Gly Gln Asn Ile Ile Lys Lys Asp Ile Gln
                405                 410                 415
Asn Met Ile Val Glu Glu Cys Gly Cys Ser
            420                 425

<210> SEQ ID NO 2
```

```
<211> LENGTH: 408
<212> TYPE: PRT
<213> ORGANISM: Homo sapiens
<220> FEATURE:
<223> OTHER INFORMATION: BMP4

<400> SEQUENCE: 2
```

| | | | | | | | | | | | | | | | |
|---|---|---|---|---|---|---|---|---|---|---|---|---|---|---|---|
| Met | Ile | Pro | Gly | Asn | Arg | Met | Leu | Met | Val | Leu | Leu | Cys | Gln | Val | |
| 1 | | | | 5 | | | | | 10 | | | | | 15 | |
| Leu | Leu | Gly | Gly | Ala | Ser | His | Ala | Ser | Leu | Ile | Pro | Glu | Thr | Gly | Lys |
| | | 20 | | | | | 25 | | | | | 30 | | | |
| Lys | Lys | Val | Ala | Glu | Ile | Gln | Gly | His | Ala | Gly | Gly | Arg | Arg | Ser | Gly |
| | | 35 | | | | | 40 | | | | | 45 | | | |
| Gln | Ser | His | Glu | Leu | Leu | Arg | Asp | Phe | Glu | Ala | Thr | Leu | Leu | Gln | Met |
| | 50 | | | | | 55 | | | | | 60 | | | | |
| Phe | Gly | Leu | Arg | Arg | Arg | Pro | Gln | Pro | Ser | Lys | Ser | Ala | Val | Ile | Pro |
| 65 | | | | | 70 | | | | | 75 | | | | | 80 |
| Asp | Tyr | Met | Arg | Asp | Leu | Tyr | Arg | Leu | Gln | Ser | Gly | Glu | Glu | Glu | Glu |
| | | | | 85 | | | | | 90 | | | | | 95 | |
| Glu | Gln | Ile | His | Ser | Thr | Gly | Leu | Glu | Tyr | Pro | Glu | Arg | Pro | Ala | Ser |
| | | | 100 | | | | | 105 | | | | | 110 | | |
| Arg | Ala | Asn | Thr | Val | Arg | Ser | Phe | His | His | Glu | Glu | His | Leu | Glu | Asn |
| | | | 115 | | | | | 120 | | | | | 125 | | |
| Ile | Pro | Gly | Thr | Ser | Glu | Asn | Ser | Ala | Phe | Arg | Phe | Leu | Phe | Asn | Leu |
| | | 130 | | | | | 135 | | | | | 140 | | | |
| Ser | Ser | Ile | Pro | Glu | Asn | Glu | Val | Ile | Ser | Ser | Ala | Glu | Leu | Arg | Leu |
| 145 | | | | | 150 | | | | | 155 | | | | | 160 |
| Phe | Arg | Glu | Gln | Val | Asp | Gln | Gly | Pro | Asp | Trp | Glu | Arg | Gly | Phe | His |
| | | | | 165 | | | | | 170 | | | | | 175 | |
| Arg | Ile | Asn | Ile | Tyr | Glu | Val | Met | Lys | Pro | Pro | Ala | Glu | Val | Val | Pro |
| | | | 180 | | | | | 185 | | | | | 190 | | |
| Gly | His | Leu | Ile | Thr | Arg | Leu | Leu | Asp | Thr | Arg | Leu | Val | His | His | Asn |
| | | | 195 | | | | | 200 | | | | | 205 | | |
| Val | Thr | Arg | Trp | Glu | Thr | Phe | Asp | Val | Ser | Pro | Ala | Val | Leu | Arg | Trp |
| 210 | | | | | 215 | | | | | 220 | | | | | |
| Thr | Arg | Glu | Lys | Gln | Pro | Asn | Tyr | Gly | Leu | Ala | Ile | Glu | Val | Thr | His |
| 225 | | | | | 230 | | | | | 235 | | | | | 240 |
| Leu | His | Gln | Thr | Arg | Thr | His | Gln | Gly | Gln | His | Val | Arg | Ile | Ser | Arg |
| | | | | 245 | | | | | 250 | | | | | 255 | |
| Ser | Leu | Pro | Gln | Gly | Ser | Gly | Asn | Trp | Ala | Gln | Leu | Arg | Pro | Leu | Leu |
| | | | 260 | | | | | 265 | | | | | 270 | | |
| Val | Thr | Phe | Gly | His | Asp | Gly | Arg | Gly | His | Ala | Leu | Thr | Arg | Arg | Arg |
| | | | 275 | | | | | 280 | | | | | 285 | | |
| Arg | Ala | Lys | Arg | Ser | Pro | Lys | His | His | Ser | Gln | Arg | Ala | Arg | Lys | Lys |
| | 290 | | | | | 295 | | | | | 300 | | | | |
| Asn | Lys | Asn | Cys | Arg | Arg | His | Ser | Leu | Tyr | Val | Asp | Phe | Ser | Asp | Val |
| 305 | | | | | 310 | | | | | 315 | | | | | 320 |
| Gly | Trp | Asn | Asp | Trp | Ile | Val | Ala | Pro | Pro | Gly | Tyr | Gln | Ala | Phe | Tyr |
| | | | | 325 | | | | | 330 | | | | | 335 | |
| Cys | His | Gly | Asp | Cys | Pro | Phe | Pro | Leu | Ala | Asp | His | Leu | Asn | Ser | Thr |
| | | | 340 | | | | | 345 | | | | | 350 | | |
| Asn | His | Ala | Ile | Val | Gln | Thr | Leu | Val | Asn | Ser | Val | Asn | Ser | Ser | Ile |
| | | | 355 | | | | | 360 | | | | | 365 | | |
| Pro | Lys | Ala | Cys | Cys | Val | Pro | Thr | Glu | Leu | Ser | Ala | Ile | Ser | Met | Leu |
| | | | 370 | | | | | 375 | | | | | 380 | | |

```
Tyr Leu Asp Glu Tyr Asp Lys Val Val Leu Lys Asn Tyr Gln Glu Met
385                 390                 395                 400

Val Val Glu Gly Cys Gly Cys Arg
                405

<210> SEQ ID NO 3
<211> LENGTH: 288
<212> TYPE: PRT
<213> ORGANISM: Homo sapiens
<220> FEATURE:
<223> OTHER INFORMATION: FGF2

<400> SEQUENCE: 3

Met Val Gly Val Gly Gly Gly Asp Val Glu Asp Val Thr Pro Arg Pro
1               5                   10                  15

Gly Gly Cys Gln Ile Ser Gly Arg Gly Ala Arg Gly Cys Asn Gly Ile
                20                  25                  30

Pro Gly Ala Ala Ala Trp Glu Ala Ala Leu Pro Arg Arg Arg Pro Arg
            35                  40                  45

Arg His Pro Ser Val Asn Pro Arg Ser Arg Ala Ala Gly Ser Pro Arg
        50                  55                  60

Thr Arg Gly Arg Arg Thr Glu Glu Arg Pro Ser Gly Ser Arg Leu Gly
65                  70                  75                  80

Asp Arg Gly Arg Gly Arg Ala Leu Pro Gly Gly Arg Leu Gly Gly Arg
                85                  90                  95

Gly Arg Gly Arg Ala Pro Glu Arg Val Gly Gly Arg Gly Arg Gly Arg
                100                 105                 110

Gly Thr Ala Ala Pro Arg Ala Ala Pro Ala Ala Arg Gly Ser Arg Pro
            115                 120                 125

Gly Pro Ala Gly Thr Met Ala Ala Gly Ser Ile Thr Thr Leu Pro Ala
        130                 135                 140

Leu Pro Glu Asp Gly Gly Ser Gly Ala Phe Pro Pro Gly His Phe Lys
145                 150                 155                 160

Asp Pro Lys Arg Leu Tyr Cys Lys Asn Gly Gly Phe Phe Leu Arg Ile
                165                 170                 175

His Pro Asp Gly Arg Val Asp Gly Val Arg Glu Lys Ser Asp Pro His
                180                 185                 190

Ile Lys Leu Gln Leu Gln Ala Glu Glu Arg Gly Val Val Ser Ile Lys
            195                 200                 205

Gly Val Cys Ala Asn Arg Tyr Leu Ala Met Lys Glu Asp Gly Arg Leu
        210                 215                 220

Leu Ala Ser Lys Cys Val Thr Asp Glu Cys Phe Phe Phe Glu Arg Leu
225                 230                 235                 240

Glu Ser Asn Asn Tyr Asn Thr Tyr Arg Ser Arg Lys Tyr Thr Ser Trp
                245                 250                 255

Tyr Val Ala Leu Lys Arg Thr Gly Gln Tyr Lys Leu Gly Ser Lys Thr
                260                 265                 270

Gly Pro Gly Gln Lys Ala Ile Leu Phe Leu Pro Met Ser Ala Lys Ser
            275                 280                 285

<210> SEQ ID NO 4
<211> LENGTH: 232
<212> TYPE: PRT
<213> ORGANISM: Homo sapiens
<220> FEATURE:
<223> OTHER INFORMATION: VEGF
```

```
<400> SEQUENCE: 4

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
        50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
                100                 105                 110

Gln Gly Gln His Ile Gly Glu Met Ser Phe Leu Gln His Asn Lys Cys
            115                 120                 125

Glu Cys Arg Pro Lys Lys Asp Arg Ala Arg Gln Glu Lys Lys Ser Val
    130                 135                 140

Arg Gly Lys Gly Lys Gly Gln Lys Arg Lys Arg Lys Lys Ser Arg Tyr
145                 150                 155                 160

Lys Ser Trp Ser Val Tyr Val Gly Ala Arg Cys Cys Leu Met Pro Trp
                165                 170                 175

Ser Leu Pro Gly Pro His Pro Cys Gly Pro Cys Ser Glu Arg Arg Lys
            180                 185                 190

His Leu Phe Val Gln Asp Pro Gln Thr Cys Lys Cys Ser Cys Lys Asn
        195                 200                 205

Thr Asp Ser Arg Cys Lys Ala Arg Gln Leu Glu Leu Asn Glu Arg Thr
    210                 215                 220

Cys Arg Cys Asp Lys Pro Arg Arg
225                 230
```